United States Patent [19]

Hill et al.

[11] 4,419,020

[45] Dec. 6, 1983

[54] MOUNTING APPARATUS

[76] Inventors: Harold I. Hill, 222 Spring Hill Rd.;
Roger W. Targowski, 216 Alma Dr.,
both of Fairfield, Conn. 06430

[21] Appl. No.: 249,531

[22] Filed: Mar. 31, 1981

[51] Int. Cl.³ ............... G01N 25/00; G01K 17/00
[52] U.S. Cl. ............................................... 374/12
[58] Field of Search ............ 73/15 B; 138/111, 112, 138/113; 374/10, 11, 12

[56] References Cited

U.S. PATENT DOCUMENTS

| | | | |
|---|---|---|---|
| 1,856,109 | 5/1932 | Murray | 138/113 |
| 3,491,581 | 1/1970 | Roberts et al. | 73/15 |
| 3,526,934 | 9/1970 | Owen, Sr. | 138/111 |
| 3,535,913 | 10/1970 | Wist | 73/15 |
| 3,590,855 | 7/1971 | Woollen | 138/111 |
| 3,667,278 | 1/1972 | Langer et al. | 73/15 |

Primary Examiner—Herbert Goldstein

[57] ABSTRACT

An apparatus for use in combination with a differential thermal analyzer includes a support member which provides at least two tangential points of contact for each of the two support columns of the instrument. Additional points of contact can also be provided by a spring clip to further secure the proper spacing of the columns.

9 Claims, 3 Drawing Figures

MOUNTING APPARATUS

BACKGROUND OF THE INVENTION

The present invention relates to a thermal analyzer and, in particular, relates to a thermal analyzer having means for rigidly positioning the elements thereof.

In general, thermal analyzers are instruments which measure the thermal absorption or emission parameters of a sample material. These parameters characterize the sample material. In practice, these parameters are most characteristic of materials when obtained during phase transitions of the sample material, i.e. when the sample material changes from one physical state, for example a solid, to a second physical state, for example a liquid. It is well settled that a phase transition is either an exothermic process or an endothermic process. Thus, the thermal energy absorbed or emitted by a sample material during a phase transition has become a widely used means for recognizing and identifying materials. In order to correctly identify a sample material, it is necessary to accurately measure the temperature changes of the sample material during the phase transition. This is usually accomplished by comparing the time rate of change of the sample temperature with the time rate of change of the temperature of a reference material when both are subjected to the same temperature profile. The reference material is selected from materials having known thermal characteristics. Both the sample and the reference are then heated according to a preselected temperature profile and the temperatures thereof are monitored. From this information, the thermal characteristics of the sample material can be obtained and the material accurately identified.

One conventional thermal analyzer is known as a differential thermal analyzer and includes a pair of double bore ceramic columns, or tubing upon which sample and reference cups are respectively located. Each cup is contacted by a thermocouple, the electrical connections to which can extend through the ceramic support columns. Since the critical measurement in a differential thermal analyzer is the temperature difference, particularly during the phase transition of the sample, between the sample and reference materials, and further, since these receptacles are enclosed in a containment member having a rather small volume of an ambient atmosphere, the relative position of the columns and the receptacles thereon is extremely important. If, during a particular measurement, for any reason, the relative position of the columns change, the entire thermal conditions within the containment member also change, i.e. the thermal system becomes dynamic rather than static. The perturbations so introduced are particularly detrimental because, as previously mentioned, the containment member encloses a relatively small volume. For these reasons it is understood that the thermal gradient distribution within the volume is quite sensitive to even a small relative movement of any of the components within that containment volume.

In addition to the pair of support columns, there is often a purge tube member extending within the containment member which can be utilized to provide a particular atmosphere therein during the analysis. The tube, when present, becomes an integral part of the interactive thermal gradient within the containment member, and thus must also be physically and thermally stable.

Presently, a conventional analyzer includes a column support member extending from a base plate, which support member has at least a pair of holes drilled therethrough through which the columns extend. Since the support columns are generally cylindrical, this arrangement results in only a single point of tangential contact between each column and its respective hole in the support member. Thus, the distance between the columns, and as a result, the distance between the sample and reference cups, can vary and thereby introduce unacceptable errors in the resultant measurements. Of course, any movement of the purge tube likewise results in erroneous measurements.

SUMMARY OF THE INVENTION

Accordingly, it is one object of the present invention to provide a thermal analyzer having a pair of support columns with means for maintaining those columns in preselected positions, which means ensures at least two points of tangential contact with each column.

Other objects and advantages of the present invention will become apparent to one skilled in the art from the following detailed specification and drawing.

DETAILED DESCRIPTION OF THE INVENTION

Figure 1:
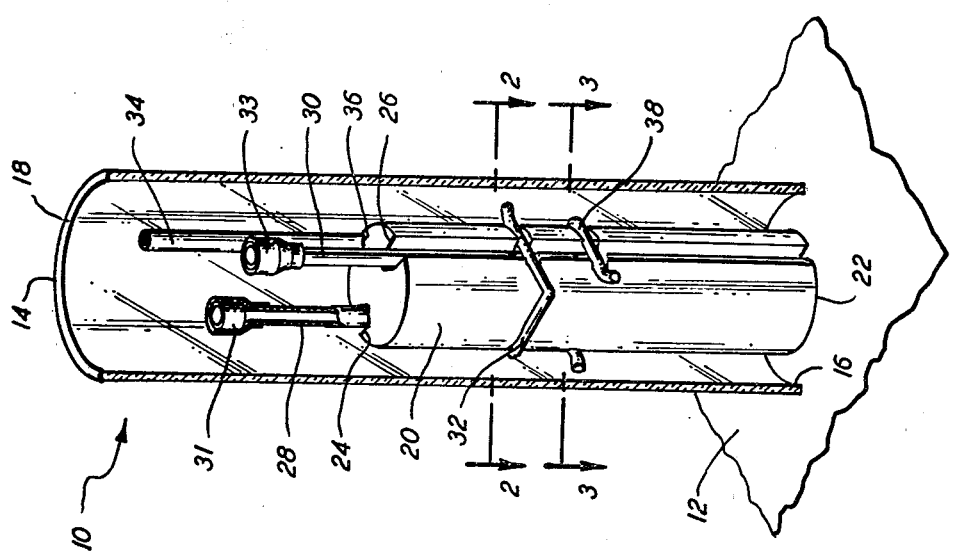
FIG. 1 is a perspective view, partially in section, of a sample chamber, not drawn to scale, embodying the principles of the present invention.

A measuring chamber, generally indicated by 10 in FIG. 1, embodying the principles of the present invention, includes a base plate 12 upon which an ambient containment member 14 is positioned. The measuring chamber 10 is surrounded by a resistance furnace, not shown, which is external to and spaced apart from the containment member 14. The containment member 14 is generally cylindrical and open at one end 16 thereof and closed at the other end 18 thereof. As shown, the one end 16 of the containment member 14 is adjacent the base plate 12 and thus defines a volume therein which is substantially sealed from the ambient atmosphere. Preferably, the containment member 14 is formed from a ceramic material, such as alumina ($Al_2O_3$), which is stable at the relatively high temperatures required for the desired tests.

A support member 20 is located within the containment member 14. The support member 20 is preferably formed of a ceramic and affixed to the base plate 12 at one end 22 thereof by means well known in the art, such as by a high temperature resistant epoxy. The support member 20 includes at least two longitudinal grooves, 24 and 26, extending thereinto from the periphery thereof. In the embodiment shown in the drawing, the support member 20 is generally a circular cylinder having a diameter on the order of about 1 centimeter and extending upwardly about 10 centimeters from the base plate 12. The particular dimensions of the grooves, 24 and 26, are further discussed hereinafter.

Figure 2:
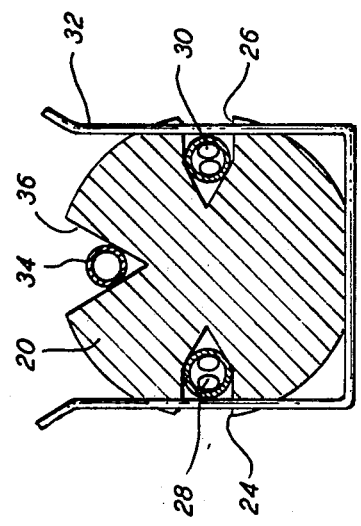
FIG. 2 is a partial cross-sectional view of the sample chamber shown in FIG. 1 taken along the line 2—2 thereof.

In addition to the support member 20, there are at least two ceramic support columns, 28 and 30, also extending from the base plate 12. In use, each column, 28 and 30, has a receptacle 31 and 33, thereon for holding the sample material and the reference material respectively. In the preferred embodiment, the double bore columns 28 and 30, have outside diameters of about 2 millimeters and extend along and within the grooves, 24 and 26 respectively, of the support member 20. The columns, 28 and 30, and the respective grooves, 24 and 26, are cooperatively dimensioned such that each column, 28 and 30, makes tangential contact with the respective groove, 24 and 26, at two points of its periphery. That is, each column, 28 and 30, peripherally contacts each side of the V portion of its respective V groove, 24 and 26 respectively. For reasons more fully described below, it is preferred that each column, 28 and 30, when properly located in its respective groove, 24 and 26, has the point of its periphery which is distal the apex of the V-groove coincident with the extended periphery of the support member 20. Such a geometric interrelationship is clearly shown in FIGS. 2 and 3.

In the embodiment shown, the assembly described above is provided with a first spring clip 32 which contacts the periphery of each support column, 28 and 30, as well as substantially all of the periphery of the support member 20. Thus, each column, 28 and 30, is urged into its respective groove, 24 and 26 respectively, and additionally provided with a third tangential point of contact to further restrict any movement thereof. The spring clip 32 is preferably formed from a stainless steel wire and slides into transverse saw cuts i.e., transverse notches intersecting the grooves, in the member 20 as shown in the drawing.

Figure 3:
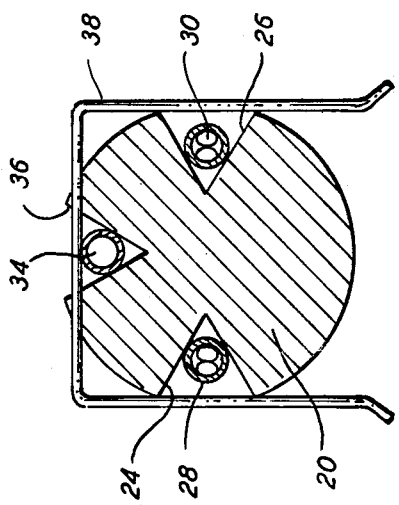
FIG. 3 is a partial cross-sectional view of the sample chamber of FIG. 1 taken along the line 3—3 thereof.

In the instance where a purge tube 34, or some other apparatus, also extends into the containment member 14, a third V-groove 36 can be formed in the support member 20. As shown in FIG. 3, the purge tube 34 can also be provided with a third point of tangential contact by a stainless steel spring clip 38, or similar means, the position of which is more clearly shown in FIG. 3.

In the preferred embodiment, the support member 20 is made from a ceramic material having grooves, 24 and 26, formed therein by known methods in the art. As the columns, 28 and 30, are, for example, 2 millimeters in diameter, the grooves, 24 and 26, are formed with an included angle of about 60° and extend perpendicularly inward into the member 20 about 3 millimeters. Such an arrangement provides the support columns, 28 and 30, with the desired two tangential points of contact which is an added dimension of stability from the prior art.

Although a specific embodiment has been described herein, other alterations and arrangements will become obvious to one skilled in the art upon the reading of the above specification. Hence, the described embodiment herein is not deemed to be limiting in any sense, and the invention is considered limited only by the appended claims and the reasonable interpretation thereof.

What is claimed is:

1. Apparatus for use in a thermal analyzer, said apparatus comprising:
    at least two spaced apart columns for supporting sample receiving receptacles extending from a base plate; and
    means for maintaining said columns a preselected distance apart and for providing at least two points of rigid contact with each said column, said means including a support member having longitudinal grooves extending thereinto from the periphery thereof; each one of said grooves being adapted to accept one of said columns thereinto and make at least two points of rigid contact therewith.

2. Apparatus as claimed in claim 1 wherein:
    said columns are cylindrical and said grooves are V-grooves.

3. Apparatus as claimed in claim 1 or 2 further including means for urging said columns into said grooves.

4. Apparatus as claimed in claim 3 wherein said means for urging provides three points of rigid tangential contact with each said column.

5. Apparatus as claimed in claim 4 wherein said means for urging is a spring clip.

6. Apparatus as claimed in claim 1 wherein said means includes means for urging said columns against said two points of rigid contact.

7. Apparatus as claimed in claim 6 wherein said urging means provides a third point of rigid contact.

8. Apparatus as claimed in claim 1 further including:
    a purge tube extending from said base plate and spaced apart from said columns, said means further providing at least two points of rigid contact for said tube.

9. Apparatus as claimed in claim 8 further including:
    means for urging at least purge tube against said two points of rigid contact.

* * * * *